United States Patent [19]

Mather et al.

[11] Patent Number: 4,790,326

[45] Date of Patent: Dec. 13, 1988

[54] METHOD AND APPARATUS FOR DETERMINING PULSE RATE

[75] Inventors: Bruce C. Mather; William C. Fox; Harry H. Peel; Dennis J. Wenzel, all of San Antonio, Tex.

[73] Assignee: Nippon Colin Co., Ltd., Komaki, Japan

[21] Appl. No.: 33,407

[22] Filed: Apr. 1, 1987

[51] Int. Cl.$^4$ ............................................. A61B 5/02
[52] U.S. Cl. .................................... 128/689; 128/706
[58] Field of Search ............................. 128/687–690, 128/702, 706, 714; 364/417

[56] References Cited

U.S. PATENT DOCUMENTS

| | | | |
|---|---|---|---|
| 3,858,574 | 1/1975 | Page | 128/689 |
| 4,022,192 | 5/1977 | Laukien | 128/706 |
| 4,195,642 | 4/1980 | Price et al. | 128/689 |
| 4,295,472 | 10/1981 | Adams | 128/690 |
| 4,301,808 | 11/1981 | Taus | 128/689 |
| 4,406,290 | 9/1983 | Walbeoffe-Wilson et al. | 128/689 |
| 4,409,983 | 10/1983 | Albert | 128/689 |
| 4,425,921 | 1/1984 | Fujisaki et al. | 128/690 |
| 4,489,731 | 12/1984 | Baumberg | 128/690 |
| 4,610,257 | 9/1986 | Furukawa | 128/689 |
| 4,664,127 | 5/1987 | Ikeyane | 128/689 |

Primary Examiner—Max Hindenburg
Attorney, Agent, or Firm—Hamilton, Smith & Clarkson

[57] ABSTRACT

A method for determining the pulse rate of a person. The method of the present invention is implemented in two phases. The first phase involes the determination of pulse intervals and the second phase provides an indication of the pulse rate based on the data produced during the first phase. The first phase is implemented by an algorithm which produces a pulse distribution profile from an array of pulses obtained from an appropriate transducer. In the second phase of the measurement, the distribution is searched to locate the region of maximum density. The pulse rate within the maximally dense region are then averaged to determine pulse rate. The pulse rate detection method of the present invention eliminates a significant number of erroneous pulse signals before calculation of pulse rate, thus providing a more accurate indication of the true pulse rate. The processing algorithm used in the preferred embodiment is based on an integer distribution the measurement can be obtained with a minimum amount of system memory and processor time.

7 Claims, 5 Drawing Sheets

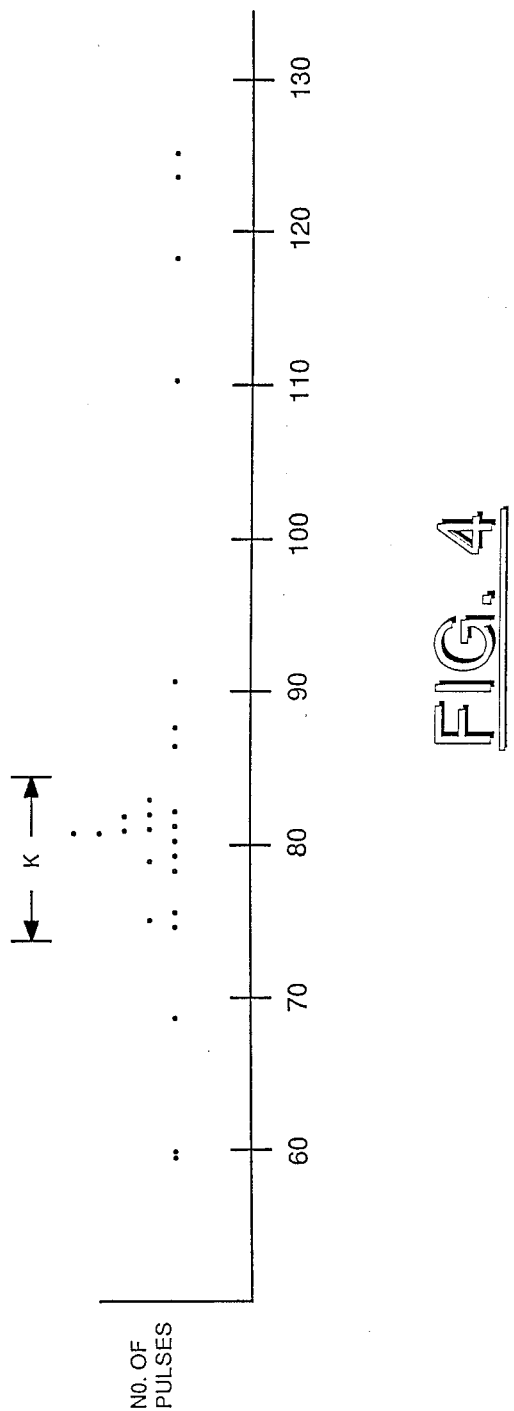

METHOD AND APPARATUS FOR DETERMINING PULSE RATE

FIELD OF THE INVENTION

The present invention relates generally to medical monitoring equipment and particularly to devices for measuring pulse rate. Specifically, the present invention provides a pulse rate detection method which can be easily implemented in a portable microprocessor-based monitoring system.

BACKGROUND

One of the parameters which is often of interest to a patient is his pulse rate. However, accurate measurement of pulse rate is often complicated by a number of factors such as arrhythmias and artifacts. For example, the erroneous detection of spurious pulses can result in a pulse rate which is erroneously high. Conversely, the failure to detect a valid pulse can lead to a pulse rate measurement which is erroneously low.

Most prior pulse rate detection systems provide an indication of pulse rate which is simply an average of pulses measured over a predetermined time interval. Such systems, therefore, tend to incorporate the above-mentioned errors into the pulse rate measurement, rather than to provide an effective means for eliminating the false data. The pulse measurement system of the present invention, described in greater detail below, provides an effective means for minimizing the effect of such errors.

SUMMARY OF THE INVENTION

The pulse rate detection method of the present invention is implemented in two phases. The first phase involves the determination of pulse intervals and the second phase provides an indication of the pulse rate based on the data produced during the first phase. The first phase is implemented by an algorithm which produces a pulse distribution profile from an array of pulses obtained from an appropriate transducer. This array contains the time positions of actual pulses as well as spurious signals which are the result of motion artifacts, cuff movement or other types of external noise detected by the system. Using the time position information, the distribution profile of the data is produced using the following procedure: (1) the pulse occurrence information is used to compute an array of integers representing the indices of accepted pulses; (2) each pulse-to-pulse time is used to compute pulse rate; and (3) the ensemble of computed pulse rates is then recorded as a distribution. In the second phase of the measurement, the distribution curve constructed as described above is searched to locate the region of maximum density. The pulse rates within this maximally dense region are then averaged to determine pulse rate.

The method of the present invention can be implemented in two possible embodiments. In one embodiment, a fixed number of pulses are stored in memory, regardless of the time frame over which the pulses occur. In an alternate embodiment, a fixed time frame is used and the number of pulses is allowed to vary. In each of these embodiments, the pulse-to-pulse interval is used to construct the pulse distribution profile.

The pulse rate detection method described above offers numerous advantages over previous rate detection methods. In particular, the invention method eliminates a significant number of erroneous signals before calculation of pulse rate. Furthermore, because the algorithm is based on an integer distribution, the measurement can be obtained with a minimum amount of system memory and processor time.

BRIEF DESCRIPTION OF THE DRAWINGS

FIG. 4 is a graphical representation of a distribution profile of pulse rate data obtained using the method of the present invention.

DETAILED DESCRIPTION OF THE PREFERRED EMBODIMENT

Figure 1:
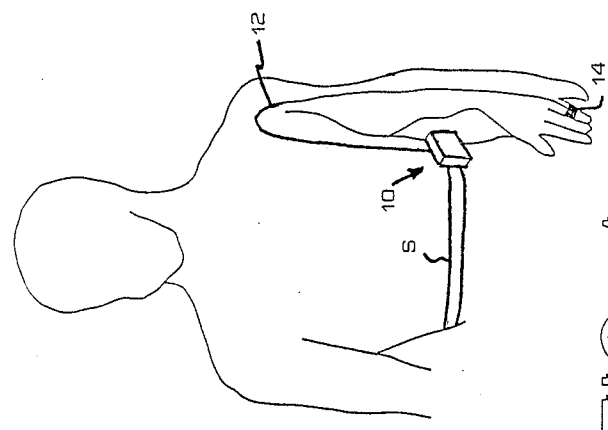
FIG. 1 is an illustration of the pulse rate measurement system of the present invention being worn by a patient.

Referring to the drawings in more detail and to FIG. 1 in particular, the pulse rate measurement system of the present invention is shown being worn by a patient. As will be discussed in greater detail below, the invention system utilizes an efficient data processing algorithm which can be implemented by a low speed microprocessor with a minimum amount of system memory. The system, therefore, is extremely compact and can be supported on the patient by a belt or strap S. Pressure measurements corresponding to the patient's pulse are obtained by a pressure transducer 14 which is in pressure communication with a blood vessel. The output signal from the pressure transducer 14 is communicated by an electrical cable 12 to the pulse rate measurement system, descrcribed in greater detail below. There are a number of pressure sensing devices, such as occlusion cuffs, which can be used to perform the function of the pressure transducer 14 shown in FIG. 1. In addition, certain types of optical transducers, such as those based on plethysmographic techniques, can be used to obtain the desired pulse data. Although the transducer 14 is shown attached to the patient's finger in FIG. 1, it will be obvious to those skilled in the art that the transducer can be placed in numerous other locations.

Figure 2:
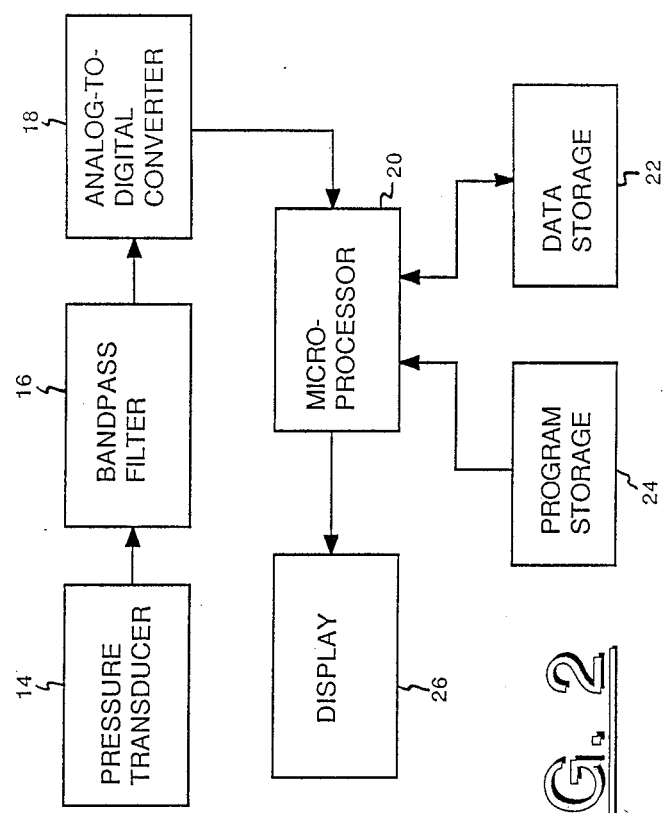
FIG. 2 is a schematic block diagram showing the major system components of the pulse rate measurement system of the present invention.

The functional features of the pulse rate measurement system 10 can be seen by referring to the simplified schematic block diagram of FIG. 2. The pressure transducer 14 produces an analog output signal corresponding to the pulsatile variations in the patient's blood vessel. The analog output signal of the pressure transducer 14 is passed through a band pass filter 16 which provides an output signal corresponding to the pulses which are of interest for determining the patient's pulse rate. The output of the band pass filter 16 is fed into the analog-to-digital converter 18 which provides a data input signal for the microprocessor 20. The microprocessor stores the pulse data in a memory device 22 and processes the data according to a computer program stored in program storage 24. The results are displayed on an appropriate display device 26, such as a light-emitting diode or liquid crystal display.

In order to perform the pulse measurement using a low speed microprocessor and limited memory, it is important that the processing routine utilize only integer arithmetic and comparisons. The computer program used in the preferred embodiment processes digitized data which is a discrete integer representation of the analog pulse signal produced by the transducer 14. The specific processing algorithm is extremely efficient in terms of processor and memory requirements, yet is effective for minimizing the effects of spurious pulses and other erroneous data signals. The steps of the processing algorithm of the preferred embodiment are described below.

During the first phase of the processing algorithm, an integer data array is constructed based on the pulse indices of pulse data which has been filtered by the band pass filter 16, and thus "accepted" as potential pulse events. As was discussed above, this array of accepted pulse indices may contain spurious pulses. The pulse occurrence time is calculated by multiplying the pulse sample index by the sample period. As an example, for a pulse sample rate of 250 Hertz, the period of 4.0 milliseconds. Each of the pulse-to-pulse intervals is used to compute a pulse rate. The ensemble of the computed pulse rates is then stored in memory as a distribution. For example, if pulse 1 is at index 10 and pulse 2 is at index 189, the difference will be 179 samples. For a sample rate of 250 Hertz, therefore, the pulse rate can be computed as (250*60)/(189−10) which gives a pulse rate of 83.8 pulses per minute. This information is then used to increment the pulse distribution profile array element corresponding to 83 pulses per minute. In the example above, the decimal portion of the calculated pulse rate is simply truncated to maintain computational efficiency. However, the algorithm could be modified to provide more sophisticated rounding at the cost of some added computation.

The procedure discussed above with regard to the interval between pulses 1 and 2 is repeated for each pulse-to-pulse interval, i.e., pulses 2–3, 3–4, etc. Using this procedure to compute the rate for pulse intervals between n pulses will result in a total of n−1 computed pulse rates. In the preferred embodiment of the present invention, only those pulses falling within a predetermined range of between 40 and 180 pulses per minute will be included in the distribution.

After the pulse distribution profile described above has been computed, a sampling window is used to locate the region of maximum pulse density. The region of maximum density is defined as the position within the distribution having the greatest number of pulses within the sample window. In cases where there are two locations having equally high pulse densities, the lower pulse rate location is chosen. This selection is made because it is more common to have additional pulses than to have missed pulses. Once the region of maximum pulse density is located, the average of the pulse rates in this region is calculated and displayed as the pulse rate.

Figure 3A:
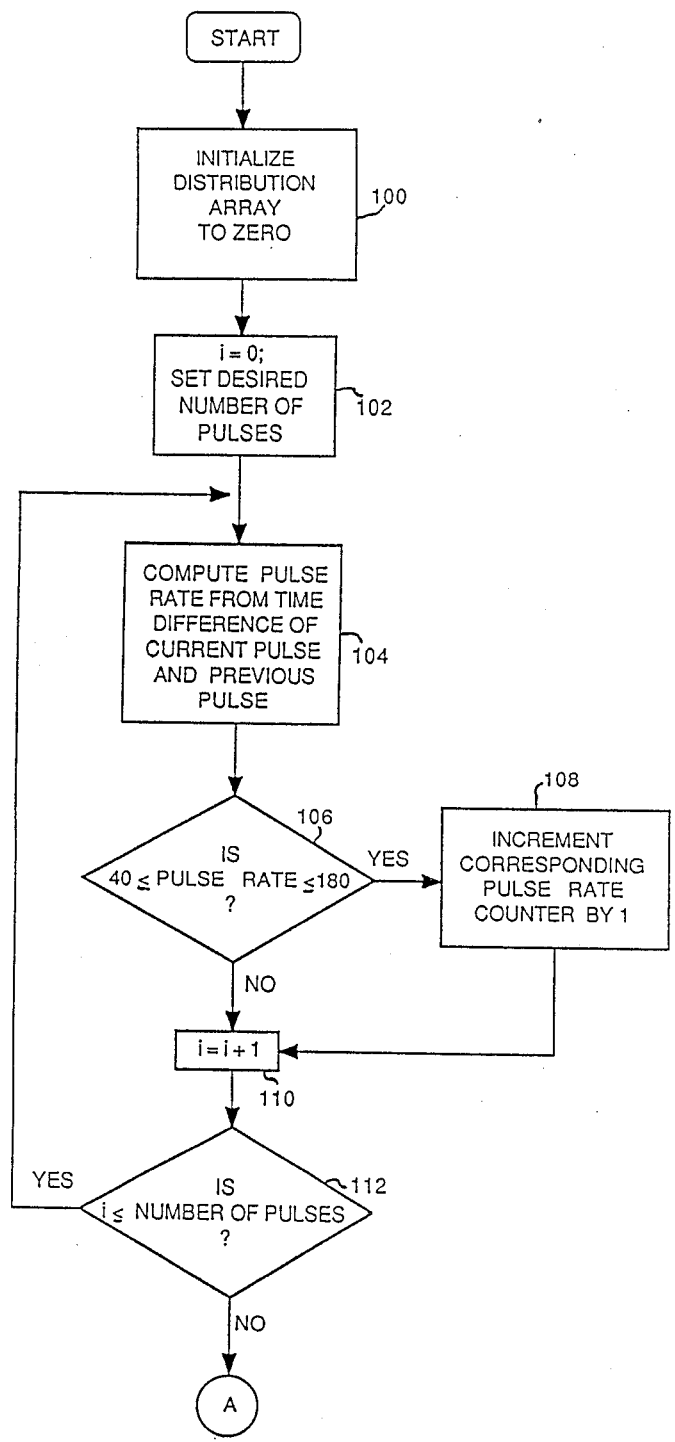
FIG. 3a is a logic flow diagram of the processing steps used in the method of the present invention to construct a pulse distribution profile of pulse data.

The general functional features of the data processing program used in the present invention are shown generally in FIGS. 3a through 3c and are summarized in the following discussion. The pulse distribution profile is constructed using processing steps 100 through 112, shown in FIG. 3a. In step 100, the array used to construct the pulse distribution profile is initialized to zero.

In step 102, the loop index counter is initialized and the number of pulses to be contained in the array is set. The pulse rate is calculated in step 104 by computing the time difference between the current pulse and the previous pulse. As was discussed above, the decimal portion of the value calculated during this step is truncated, although processing steps could be added to provide a more sophisticated rounding scheme. In step 106, a comparison is made to determine whether the pulse rate calculated in step 104 is within the predetermined limits of 40 and 180 pulses per minute. If the pulse falls within these limits, the pulse rate counter corresponding to the computed pulse rate is incremented in step 108. In step 110, the loop counter index, i, is incremented by one and in step 112 the new value of this counter is compared to the preset number of pulses to determine whether all of the pulses have been processed. If the loop counter is less than or equal to the preset number of pulses, the program returns to step 104 for further processing. However, if all of the pulses have been processed, the pulse distribution array has been successfully constructed and the search for maximum pulse density is initiated.

Figure 3B:
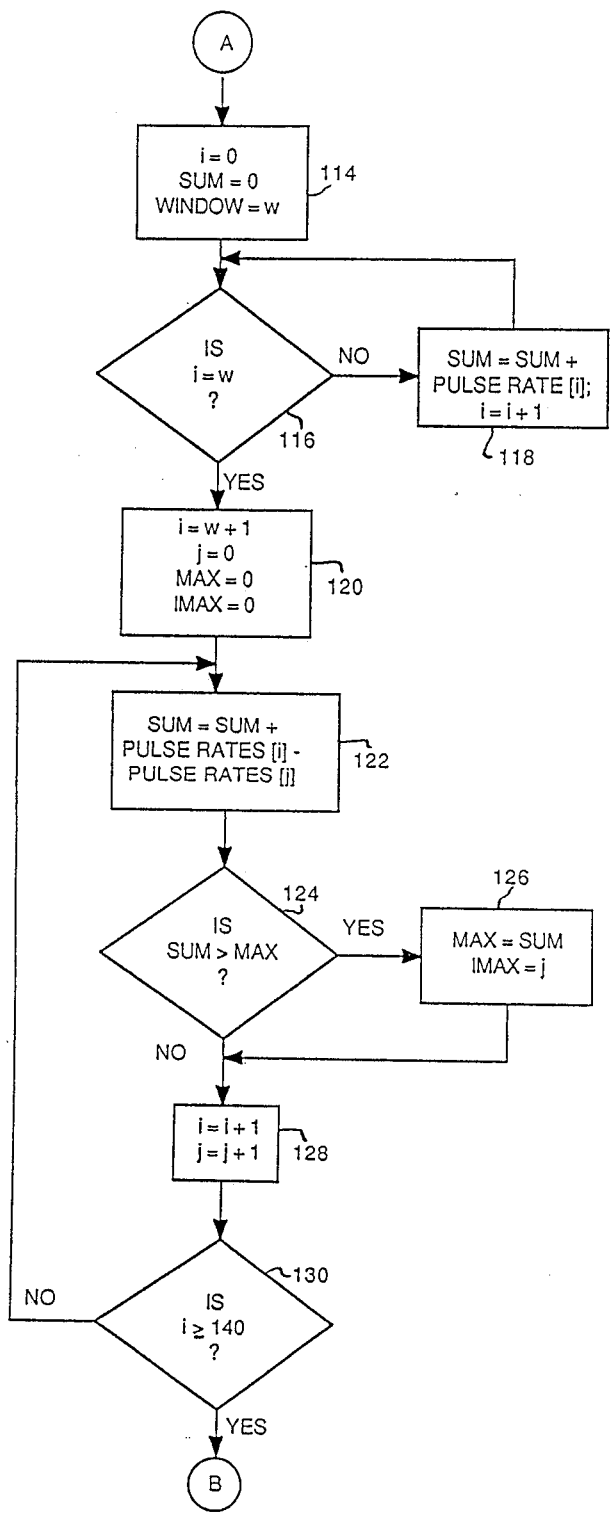
FIG. 3b is a logic flow diagram of the processing steps used in the method of the present invention to locate the region of maximum pulse density in the pulse distribution profile.

The search for maximum pulse density is accomplished by processing steps 114 through 130, shown in FIG. 3b. In step 114, the loop counter and a summation variable are initialized to zero and a window size, w, is established. The size of the window can vary over a fairly wide range, but generally has a width of between 5 and 20 indices. In the preferred embodiment, a window size of 9 is used. In step 116, the loop counter, i, is compared to the window size, w, to determine if enough data has been processed to satisfy the preset criterion for window size. A summing algorithm is used in step 118 to calculate a pulse rate for all of the pulse indices currently in the window. This summation is continued until the comparison criterion of step 116 is satisfied. The program then proceeds to step 120 in which a running sum algorithm is initiated. In this step, indices and counters are initialized for determining the maximum value and the location of the maximum value of the points in the pulse distribution profile currently in the window. In step 122, the sum of the data in the window is computed. This value is compared, in step 124, to the previous maximum value to determine if a new maximum value has been located. If the calculated sum is greater than the previous maximum, the previous maximum value is replaced with the calculated sum in step 126 and the location corresponding to the new maximum is stored. The window is then moved over one point by incrementing the loop counters i and j, as shown in step 128. In step 130, the value of the counter, i, is compared to a preset upper limit of 140, which corresponds to a pulse rate of 180. If this limit has not been reached, the program returns to step 122; otherwise, the program proceeds to the calculation of average pulse rate.

Figure 3C:
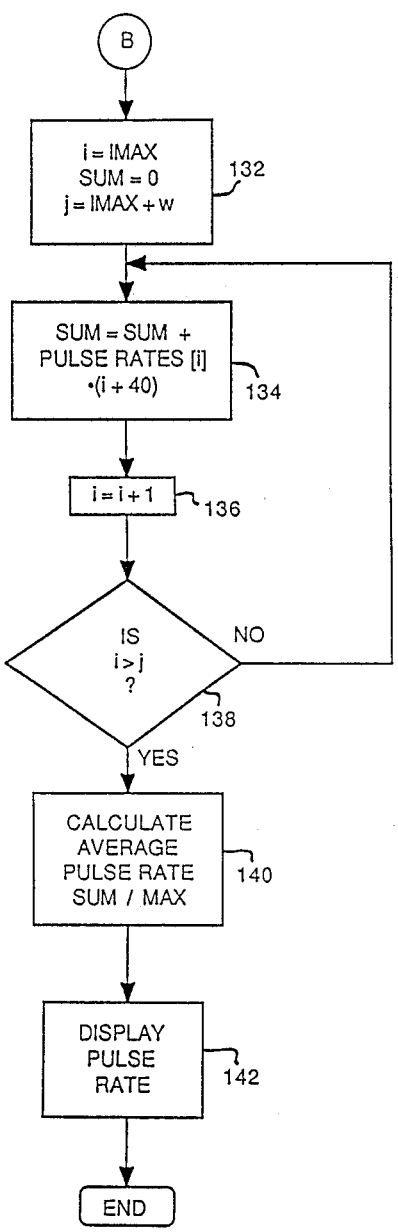
FIG. 3c is a logic flow diagram of the processing steps used in the method of the present invention to calculate an average pulse rate in the region of the distribution profile having maximum pulse density.

The determination of average pulse rate is accomplished by processing steps 132 through 140, shown in FIG. 3c. In step 132, the maximum density window located above is defined by a starting index, i, and an ending index, j, and the sum value for the window is initialized to zero. The pulse-to-pulse time differences within this window are summed in step 134. The value of the index, i, in this calculation is incremented by 40 in order to have the array elements 0 through 140 correspond to pulse rates of 40 to 180, as defined in the first phase of the program. In step 136, the index, i, is incremented to move to the next position in the array and in step 138, the value of i is tested to determine if all data points within the window have been processed. If the test indicates that additional data remains, the program returns to step 134 to process the next data point, However, if the test indicates that all of the data has been processed, then the average pulse rate is calculated in step 140 and displayed in step 142. The pulse rate calculated in step 140 is the weighted average of the pulse-to-pulse time differences within the window.

FIG. 4 is a graphical representation of a pulse rate distribution profile obtained using the above-described processing algorithm. The region illustrated by the reference letter K represents the region of maximum pulse density which is averaged to obtain the measurement of the patient's pulse rate. In prior pulse rate measurement systems, spurious pulse data, such as that in the region between 110 and 120, and erroneous pulse data, such as that below 60 pulses per minute, would be incorporated into the pulse measurement. In the pulse measurement system of the present invention, however, these spurious and erroneous pulse signals are removed before calculation of the pulse rate, thus providing a more accurate indication of the pulse rate.

In embodiment of the processing algorithm discussed above, the pulse rate is determined from a fixed number of pulses stored in memory, regardless of the time frame over which the pulses occur. In an alternate embodiment, a fixed time frame is used and the number of pulses is allowed to vary. In this embodiment of the method, the pulse-to-pulse interval is still used to construct the pulse distribution profile.

Although the method and apparatus of the present invention has been described in connection with the preferred embodiment, it is not intended to be limited to the specific form set forth herein, but, on the contrary, it is intended to cover such alternatives and equivalents as can reasonably be included within the spirit and scope of the invention as defined by the appended claims.

What is claimed is:

1. A method for determining the pulse rate of a person, comprising the steps of:
    obtaining a set of data corresponding to pulsatile variations in a blood vessel of said person;
    processing said data to obtain a pulse distribution profile of said pulse rates, said step of processing said data comprising the steps of forming an array of time position indices corresponding to the said data points and calculating pulse rates for each of said time position indices;
    locating the region of maximum density in said pulse distribution profile; and
    determining said person's pulse rate from said region of maximum density in said pulse distribution profile.

2. The method according to claim 1, said step of locating said region of maximum pulse density comprising the step of sampling said pulse distribution profile with a moving window summing algorithm, said moving window having a predetermined width of between 5 and 20 indices.

3. The method according to claim 2, said step of correlating said region of maximum pulse density with said person's pulse rate further comprising the step of averaging the pulse rates in said region of maximum density.

4. A method of determining the pulse rate of a person, comprising the steps of:
    obtaining a set of data points corresponding to pulsatile variations detected by a transducer in pressure communication with a blood vessel of said person, said data set containing actual pulse data and spurious pulse data;
    processing said data set to obtain an array of time position indices corresponding to said pulsatile variations;
    calculating pulse rates for each of said time position indices;
    forming a pulse distribution profile of said pulse rates;
    locating the region of maximum density in said pulse distribution profile, said spurious pulse data being substantially eliminated from said region of maximum density; and
    computing a weighted average of the pulse rates in said region of maximum density to obtain an indication of the person's pulse rate.

5. The method according to claim 4, said step of locating said region of maximum pulse density comprising the step of sampling said pulse distribution profile with a moving window summing algorithm, said moving window having a predetermined width.

6. The method according to claim 5, said window having a width of between 5 and 20 indices.

7. The method according to claim 6, said window having a width of nine indices.

* * * * *